United States Patent [19]

Margalit

[11] Patent Number: 5,401,511
[45] Date of Patent: Mar. 28, 1995

[54] BINDING OF PROTEIN AND NON-PROTEIN RECOGNIZING SUBSTANCES TO LIPOSOMES

[75] Inventor: Rimona Margalit, Givataim, Israel

[73] Assignee: Baxter International Inc., Deerfield, Ill.

[21] Appl. No.: 960,196

[22] Filed: Oct. 9, 1992

Related U.S. Application Data

[63] Continuation of Ser. No. 655,878, Feb. 14, 1991, abandoned.

[51] Int. Cl.⁶ .............................................. A61K 9/127
[52] U.S. Cl. .................... 424/450; 428/402.2
[58] Field of Search ...................... 424/450; 428/402.2; 264/4.1, 4.3, 4.6; 260/403; 836/829

[56] References Cited

U.S. PATENT DOCUMENTS

| | | | |
|---|---|---|---|
| 4,485,054 | 11/1984 | Mezei et al. | 264/4.6 |
| 4,708,861 | 11/1987 | Popescu | 424/457 |
| 4,761,288 | 8/1988 | Mezei et al. | 424/450 |
| 4,839,175 | 6/1989 | Guo et al. | 424/450 |

FOREIGN PATENT DOCUMENTS

| | | |
|---|---|---|
| A-85742/91 | 4/1992 | Australia . |
| 210013 | 11/1984 | Japan . |
| 8911270 | 11/1989 | WIPO . |
| WO90/07924 | 7/1990 | WIPO . |
| WO90/11069 | 10/1990 | WIPO . |
| WO92/13525 | 8/1992 | WIPO . |

OTHER PUBLICATIONS

Chapter 6 of vol. III from Liposome Technology (Gregoriadis, Editor; CRC Press, Publisher; 1984; chapter on "Immobilization of Specific Proteins on Liposome Surface: Systems for Drug Targeting".
Publication from vol. 160, No. 2, 1989 of Biochemical and Biophysical Research Communications titled "Preparation of EGF Labeled Liposomes and Their Uptake By Hepatocytes".
Publication from Methods in Enzymology, vol. 70, 1980 (Reichlin, author; Academic Press, Inc., publisher) titled "Use of Glutaraldehyde as a Coupling Agent for Proteins and Peptides".
Torchillin in Liposome Technology III, p. 75 1984.
Wessig et al in Die Pharmazic 45 (1990) p. 849.
Excerpt from Patent Abstracts of Japan, vol. 9, No. 74 (C-273) (1797) dated Apr. 3, 1985.
German publication authored by V. Weissig et al, titled "Kovalente Bindug von Peptiden an liposomale Oberflachen"; pp. 849-850 of Pharmazie, vol. 45 No. 11, dated Nov. 1990.
International Application No. PCT/EP89/00521 published on Nov. 30, 1989.
International Application No. PCT/EP87/01833 published on Feb. 11, 1988.
International Application No. PCT/FR90/00176 published on Oct. 4, 1990.

*Primary Examiner*—G. S. Kishore
*Attorney, Agent, or Firm*—Wallenstein, Wagner & Hattis, Ltd.

[57] ABSTRACT

Methodologies have been developed and certain recognizing substances and crosslinking reagents have been identified to modify liposomes. Crosslinking reagents link residues on the liposomal surface to the residues offered by certain recognizing substances. The crosslinking reagents include glutaraldehyde (GAD) and a water soluble carbodiimide, preferably, 1-ethyl-3-(3-dimethylaminopropyl) carbodiimide (EDC). The recognizing substances include gelatin, collagen, and hyaluronic acid (HA). Following these methodologies, recognizing substances can be utilized as an adhesive or glue to attach the liposomes onto a target area. These "bioadhesive" liposomes offer potential advantages as a microscopic drug delivery system.

4 Claims, No Drawings

BINDING OF PROTEIN AND NON-PROTEIN RECOGNIZING SUBSTANCES TO LIPOSOMES

This application is a continuation of U.S. Ser. No. 07/655,878, filed on Feb. 14, 1991, now abandoned.

BACKGROUND OF THE INVENTION

The present invention relates to the preparation of microscopic drug delivery systems (MDDS) utilizing drug-encapsulating bioadhesive liposomes.

Microscopic drug delivery systems (MDDS) have been developed for improved drug administration relative to administration of drugs in their free form. Drug-loaded MDDS can perform as sustained or controlled release drug depots. By providing a mutual protection of the drug and the biological environment, MDDS reduces drug degradation or inactivation. As a system for controlled release of a drug, MDDS improves drug efficacy and allows reduction in the frequency of dosing. Since the pharmacokinetics of free drug release from depots of MDDS are different than from directly-administered drug, MDDS provides an additional measure to reduce toxicity and undesirable side effects.

MDDS is divided into two basic classes: particulate systems, such as cells, microspheres, viral envelopes and liposomes; or nonparticulate systems which are macromolecules such as proteins or synthetic polymers. Liposomes have been studied as drug carriers and offer a range of advantages relative to other MDDS systems. Composed of naturally-occurring materials which are biocompatible and biodegradable, liposomes are used to encapsulate biologically active materials for a variety of purposes. Having a variety of layers, sizes, surface charges and compositions, numerous procedures for liposomal preparation and for drug encapsulation within them have been developed, some of which have been scaled up to industrial levels. Liposomes can be designed to act as sustained release drug depots and, in certain applications, aid drug access across cell membranes. Their ability to protect encapsulated drugs and various other characteristics make liposomes a popular choice in developing MDDS, with respect to the previous practices of free drug administration.

Despite the advantages offered, utilization of drug-encapsulating liposomes does pose some difficulties. For example, liposomes as MDDS have limited targeting abilities, limited retention and stability in circulation, potential toxicity upon chronic administration and inability to extravasate. In recent years, successful attempts have been made to bind different substances to liposomes. For example, binding of chymotrypsin to liposomes has been studied as a model for binding substances to liposomal surfaces. Recognizing substances, including antibodies, glycoproteins and lectins, have been bound to liposomal surfaces in an attempt to confer target specificity to the liposomes. Concentrating on systemic application and in vivo studies, these previous efforts have discussed methods of binding recognizing substances with liposomes and studied the effectiveness of such modified liposomes. Although the bonding of these recognizing substances to liposomes occurred, the resulting modified liposomes did not performed as hoped, particularly during in vivo studies. Other difficulties are presented when utilizing these recognizing substances. For example, antibodies can be patient specific and therefore, add cost to the drug therapy.

The number and surface density of the discrete sites on the liposomal surfaces for covalent bonding are dictated by the liposome formulation and the liposome type. The liposomal surfaces also have sites for non-covalent association. Covalent binding is essential as noncovalent binding might result in dissociation of the recognizing substances from the liposomes at the site of administration since the liposomes and the bioadhesive counterparts of the target site (that is, the bioadhesive matter) compete for the recognizing substances. Such dissociation would reverse the administered modified liposomes into regular, non-modified liposomes, thereby defeating the purpose of administration of the modified liposomes.

To form covalent conjugates of recognizing substances and liposomes, crosslinking reagents have been studied for effectiveness and biocompatibility. Once such reagent is glutaraldehyde (GAD). Through the complex chemistry of crosslinking by GAD, linkage of the amine residues of the recognizing substances and liposomes is established. For example, previous efforts have studied binding of chymotrypsin and liposomes with GAD as the crosslinking reagent. Further, covalently binding a growth factor as a recognizing substance to liposomes has been disclosed in my concurrently filed application.

SUMMARY OF INVENTION

According to the present invention, methodologies have been developed and recognizing substances and crosslinking reagents have been identified to modify liposomes for MDDS. More specifically, crosslinking reagents have been identified which crosslink residues on tile liposomal surface to the residues offered by certain recognizing substances. The crosslinking reagents include glutaraldehyde (GAD) and a water soluble carbodiimide, preferably, 1-ethyl-3-(3-dimethylamino-propyl) carbodiimide (EDC). The recognizing substances include gelatin, collagen, and hyaluronic acid (HA). Following these methodologies, recognizing substances can be utilized as an adhesive or glue to attach the liposomes onto a target area. These "bioadhesive" liposomes offer potential advantages as a MDDS for the administration of drugs which is further disclosed in my concurrently filed applications.

DETAILED DESCRIPTION

According to the present invention, various recognizing substances have been covalently bound to liposomal surfaces through the chemistry of crosslinking functional groups offered by the recognizing substances and the liposomes. Liposomes, in particular, multilamellar vesicles (MLV), microemulsified liposomes (MEL) or large unilamellar vesicles (LUVET), each containing phosphatidylethanolamine (PE), have been prepared by established procedures. The inclusion of PE in the liposome formulations provides an active functional residue, a primary amine, on the liposomal surface for crosslinking purposes.

Recognizing substances have been successfully linked with PE-liposomes. Using commercially available gelatin and collagen, these protein-recognizing substances were linked to the liposomes through amine residues. HA is a natural polymer with alternating units of N-acetyl glucoseamine and glucoronic acid. Using a crosslinking reagent, HA offers carboxylic acid residues as functional groups for covalent binding. The N-acetyl-glucoseamine contains hydroxyl units of the type —$CH_2$—OH which can be oxidized to aldehydes, thereby offering an additional method of crosslinking HA to the liposomal surface in the absence of a crosslinking reagent.

The "level of covalent binding" as reported in the Examples and Tables 1-4, is defined as the quantity of recognizing substance bound to a given quantity of lipid in the final product since the most accurate quantitative measure of liposomes is in terms of lipid quantities. The recognizing substances and lipids are assayed by traces of labels included in each formulation. Alternatively, the lipids are assayed by colorimetric methods. The determination of the protein-recognizing substances can be done by the Lowry procedure previously reported. Free HA and liposome bound HA is determined by the Alcian Blue method.

For a given lipid quantity, different liposome types will yield different quantities of liposomes. Therefore, similar initial ratios of recognizing substance to lipid for different liposome types should not be expected to yield the same level of binding. Another factor which would yield different results for different liposomes even under the same initial recognizing substance to lipid ratios, is the differences in particle size, therefore in curvature, number and accessibility or PE sites on the surface of the liposome. Therefore, comparisons among liposome types should be avoided.

EXAMPLE ONE

Gelatin is added to a PE-liposome sample and the mixture is buffered by a phosphate buffer saline solution (PBS) to pH of 7.2. Concentration ratios of gelatin to lipid are shown in Table 1. Aliquots from a 25% solution of the crosslinking reagent GAD are added at a ratio of 10 µl per 1 ml gelatin/PE-liposome mixture. Incubation for a desired period is completed at either room temperature without stirring or at 37° C. with stirring. Depending upon the liposome used, excess unreacted material was removed through either centrifugation and washings, column chromatography or dialysis against PBS.

TABLE 1

| GELATIN-LIPOSOME CROSSLINKING BY GAD | | | |
|---|---|---|---|
| Liposome | ug Gelatin/uMole Lipid | | Incubation |
| Type | Initial | Final | Period (a) |
| MEL | 21 | 0.02 | Short |
| MEL | 63 | 0.24 | Short |
| MEL | 127 | 0.26 | Short |
| MEL | 21 | 15 | Long |
| MEL | 23 | 14 | Long |
| MEL | 25 | 18 | Long |
| MEL | 63 | 43 | Long |
| MEL | 187 | 208 | Long |
| MLV | 18 | 0.24 | Long |
| MLV | 66 | 0.67 | Long |
| MLV | 281 | 2.6 | Long |
| MLV | 556 | 6.4 | Long |
| MLV | 1140 | 13 | Long |
| MLV | 2350 | 13 | Long |
| MLV | 3440 | 24 | Long |
| MLV | 5830 | 26 | Long |

(a) Incubation Periods: "Short" is 5 minutes; "Long" is 24-48 hours.

EXAMPLE TWO

Collagen is crosslinked to PE-MLV samples with GAD following the same procedure as in Example 1, at "Long" incubation periods.

TABLE 2

| COLLAGEN-LIPOSOME CROSSLINKING BY GAD | | |
|---|---|---|
| Liposome | ug Collagen/uMole Lipid | |
| Type | Initial | Final |
| MLV | 1.64 | 0.90 |
| MLV | 2.06 | 1.18 |
| MLV | 5.01 | 2.20 |
| MLV | 8.96 | 5.07 |
| MLV | 9.83 | 6.78 |
| MLV | 9.86 | 6.02 |
| MLV | 10.68 | 8.20 |
| MLV | 18.79 | 11.55 |
| MLV | 20.00 | 14.14 |

EXAMPLE THREE

Aqueous solutions of HA and of EDC were mixed to yield a preparation system of HA and EDC each at final concentrations of 1.7 mg/ml. The pH of the preparation system was adjusted to 3 by titration with 1N HCl. The preparation system was incubated for a time period at 37° C. with stirring. Table 3 shows an example of variation in the pre-incubation time period for reacting HA with EDC. A pre-incubation period of 3 hours is preferred to activate the carboxylic residues of HA.

TABLE 3

| EFFECTS OF PRE-INCUBATION HA-LIPOSOME BINDING(a) | |
|---|---|
| PRE-INCUBATION PERIOD (hours) | mg HA Bound/mmole Lipid |
| 0 | 0 |
| 1 | 0 |
| 3 | 22.8 ± 0.9 |
| 24 | 20.9 ± 2.8 |

(a) Liposomes are LUVET, incubation was at 37° C., incubation of complete reaction mixture at pH 3 with the addition of borate buffer for 24 hours.

After the pre-incubation period, PE-liposome samples were added and followed by the addition of a 0.1M borate buffer at pH 8.5. The HA/PE-liposome mixture was incubated at 37° C. in a shaker bath for 24 hours. Removal of excess unbound HA and reagents was by ultracentrifugation and washings. Initial and final concentrations of HA/lipid are reported in Table 5.

EXAMPLE FOUR

Various parameters affect the successful binding of HA to PE-liposomes when using EDC as the crosslinking reagent. These parameters include a pre-incubation procedure, pH of the reaction mixture, use of buffer solution in the incubation system and the contact area between liposomes and HA. Tables 4 and 5 provide data on variations of these parameters.

TABLE 4

| EFFECTS OF pH, BUFFER, PRE-INCUBATION AND CONTACT AREA ON COVALENT BONDING OF HA AND LIPOSOMES(a) | | | |
|---|---|---|---|
| pH | Borate Buffer | HA-Liposome Contact Area | mg HA Bound/ mmole Lipid |
| 4.5(b) | — | Narrow | 3.1 ± 0.6 |
| 4.5 | — | Narrow | 5.2 ± 0.5 |
| 4.5 | — | Wide | 7.6 ± 3.9 |
| 4.5 | Added | Wide | 19.0 ± 0.9 |
| 3.0 | Added | Wide | 26.5 ± 0.9 |

(a)Using MLV and EDC, three hours of pre-incubation (see exception below), 24 hours incubation of complete reaction mixture, both at 37° C.
(b)No pre-incubation, pH listed is for the incubation of the complete reaction mixture.

EXAMPLE FIVE

A reaction mixture of HA, dimethyl sulfoxide (DMSO) and acetic anhydride were stirred at room temperature for 24 hours. At the end of this period, the mixture was transferred to a dialysis sac and dialyzed against water over 48 hours. Activated HA was completely recovered from the sac as determined by the Alcian Blue method. Activated HA was incubated with PE-liposomes in 0.5M carbonate buffer at a pH of 9 for 24 hours in a shaker bath at 37° C. Adding sodium borohydride as a reducing agent, portions of the activated HA/PE-liposome mixture were incubated for an additional two hours. Removal of excess unbound HA and reagents was by centrifugation and washings. Concentration ratios of activated-HA to lipid are shown in Table 5.

TABLE 5

COVALENT BINDING OF HA TO LIPOSOMES
CROSSLINKER-HA & ACTIVATED-HA (a)

| Methodology | mg HA/mmoles Lipid | | pH |
|---|---|---|---|
| | Initial | Final | |
| With EDC | 1000 | 27 | 3 |
| Activated HA with Reduction | 974 | 86 | 9 |
| Activated HA without Reduction | 974 | 113 | 9 |

(a) Liposomes were MLV

The covalent bonding of the recognizing substances, gelatin, collagen and HA, to liposomal surfaces can be achieved. Noncovalently bound product is removed as excess unreacted material and does not appear in the reported results. Preferably, protein-recognizing substances such as gelatin and collagen, are covalently bonded to PE-liposomes through amine residues with the crosslinking reagent GAD.

The bonding of HA to PE-liposomes can be completed either in the presence or absence of a crosslinking reagent. In the presence of a reagent, preferably EDC, a pH of 3 in the pre-incubation system is preferred. A 3-hour approximate time period is preferred for pre-incubation of the HA and crosslinking reagent. The addition of a 0.1M borate buffer at pH of 8.5 to the incubation system offers a positive contribution to the binding step. Changing the reaction mixture vessel in the binding step from test tubes to flasks, thereby increasing the area of contact between liposomes and HA did not adversely effect the binding results.

Bonding of HA to PE-liposomes without a crosslinking reagent is preferably completed by pre-activation of HA and an incubation period of 24 hours at a reaction mixture pH of 9.

While the preferred embodiments have been described, various modifications and substitutes may be made without departing from the scope of the invention. For example, the pre-activation of the carboxylic residues of HA could be completed with dicyclohexylcarbodiimide or with N,N'-disuccinimidyl carbonate. Accordingly, it is to be understood that the invention has been described by way of illustration and not limitation.

What I claim is:

1. A modified liposome comprising a liposome having phosphatidylethanolamine as a provider of a primary amine residue covalently linked by a crosslinking reagent to a target recognizing substance which is hyaluronic acid.

2. The modified liposome of claim 1 wherein the liposome and hyaluronic acid are covalently linked by glutaraldehyde.

3. The modified liposome of claim 1 wherein the liposome and hyaluronic acid are crosslinked with 1-ethyl-3 (3-dimethylaminopropyl) carbodiimide.

4. The modified liposome of claim 1 wherein the target recognizing substance consists of an activated hyaluronic acid created by incubation of hyaluronic acid with dimethyl sulfoxide and acetic anhydride, then reacting the activated hyaluronic acid with liposomes.

* * * * *